US00PP31441P3

(12) United States Plant Patent
Conev

(10) Patent No.: US PP31,441 P3
(45) Date of Patent: Feb. 18, 2020

(54) SHRUB ROSE PLANT NAMED 'VLR002'

(50) Latin Name: *Rosa hybrida*
Varietal Denomination: VLR002

(71) Applicants: Vineland Research and Innovation Centre, Vineland Station, Ontario (CA); Canadian Nursery Landscape Association, Milton, Ontario (CA)

(72) Inventor: Rumen Conev, Vineland Station (CA)

(73) Assignees: Vineland Research and Innovations Centre Inc., Vineland Station, Ontario; Canadian Nursery landscape Association, Milton, Ontario ( * ) Notice: Subject to any disclaimer, the term of this patent is extended or adjusted under 35 U.S.C. 154(b) by 0 days.

(21) Appl. No.: 16/350,712

(22) Filed: Dec. 27, 2018

(65) Prior Publication Data

US 2019/0215998 P1 Jul. 11, 2019

(30) Foreign Application Priority Data

Jan. 11, 2018 (CA) ..... PBR 18-9372

(51) Int. Cl.
*A01H 5/02* (2018.01)
*A01H 6/74* (2018.01)

(52) U.S. Cl.
USPC ..... Plt./108
CPC ..... *A01H 6/749* (2018.05)

(58) Field of Classification Search
USPC ..... Plt./108
See application file for complete search history.

*Primary Examiner* — Anne Marie Grunberg
(74) *Attorney, Agent, or Firm* — Buchanan Ingersoll & Rooney PC

(57) ABSTRACT

A new and distinct variety of shrub rose plant herein referred to by its cultivar name, 'VLR002', is provided that abundantly forms on a continuous basis attractive double formed, red colored blossoms. The plant exhibits semi-upright bush growth habit and dark green foliage is formed. Resistance to black spot disease is displayed. The plant is well suited for providing attractive ornamentation in the landscape.

7 Drawing Sheets

Figure 1:
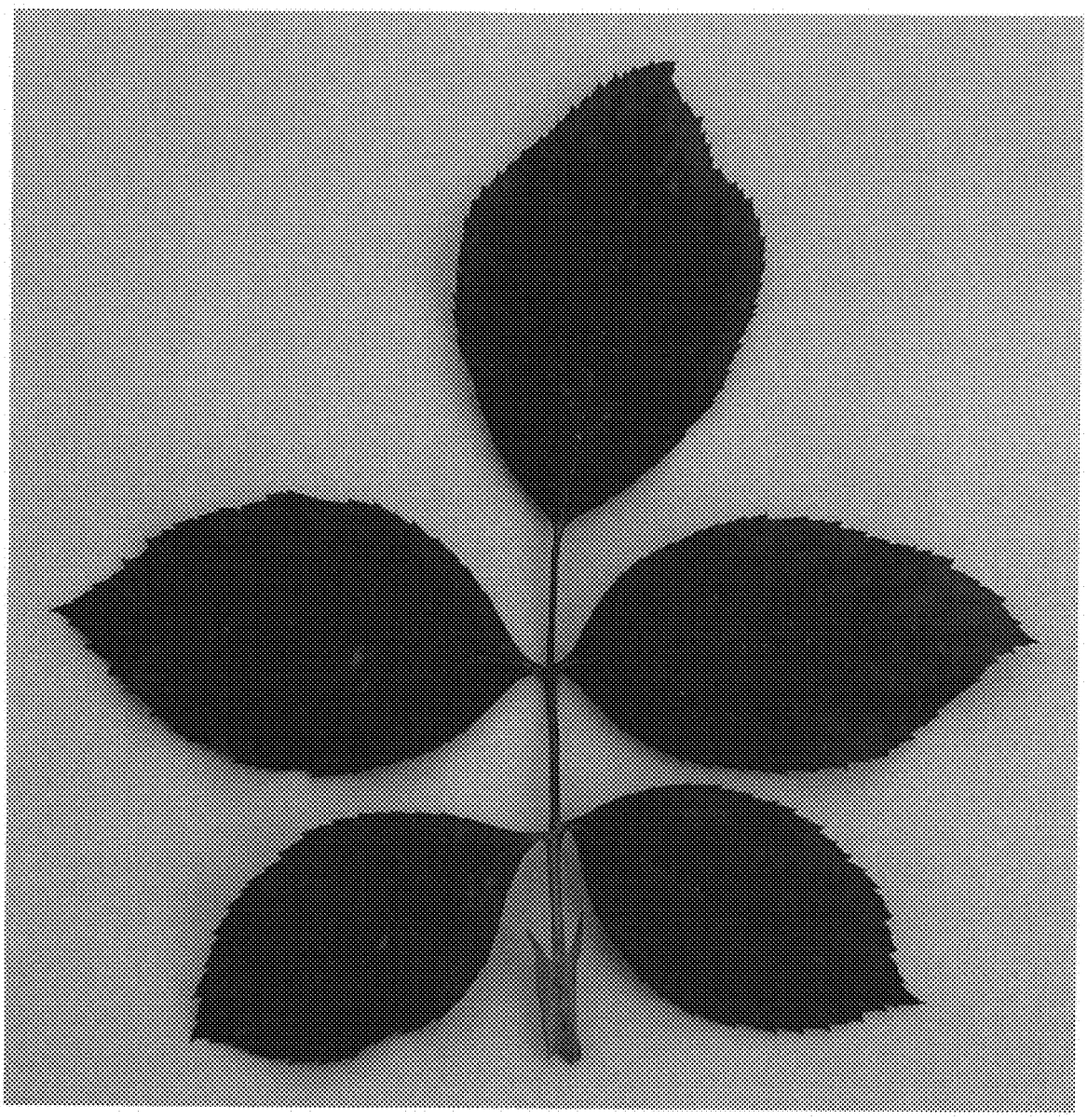

Botanical/commercial classification:
Latin name—*Rosa hybrida.*
Common name—Shrub Rose Plant.
Varietal denomination: 'VLR002'.

CROSS-REFERENCE TO RELATED APPLICATIONS

This application claims priority Plant Breeders' Rights Application Number 18-9372, which was filed in Canada on Jan. 11, 2018, of which the content of is hereby expressly incorporated by reference in its entirety for all purposes.

SUMMARY OF THE INVENTION

The new and distinct variety of *Rosa hybrida* shrub rose plant was created in 2012 in Vineland, Ontario, Canada by artificial pollination wherein two parents which previously had been studied were crossed in the hope that they would contribute the desired characteristics. The female parent (i.e., the seed parent) of the new variety was the '60' variety (non-patented). The male parent (i.e., the pollen parent) was the '564' variety (non-patented in the United States).

The parentage of the new variety can be summarized as follows:

'60' x '564'.

The seeds resulting from the above pollination were sown and small plants were obtained which were physically and biologically different from one another. Seedlings were evaluated and a single seedling possessing desired characteristics was identified.

It was found that the new shrub rose plant of the present invention possesses the following combination of characteristics:

(a) abundantly and continuously forms attractive double formed red blossoms,
(b) exhibits a semi-upright bush growth habit,
(c) forms attractive dark green foliage, and
(d) is well suited for growing as attractive ornamentation in the landscape.

The new variety well meets the needs of the horticultural industry and can be grown to advantage in the landscape, including parks, gardens, public areas, and residential landscapes, where attractive ornamentation is to be provided.

The new variety can be readily distinguished from its ancestors. More specifically, while 'VLR002' displays red colored flowers, the '60' variety (i.e., the seed parent) displays dissimilar red colored flowers and the '564' variety (i.e., the pollen parent) displays dissimilar light yellow colored flowers. In addition, the new variety displays larger leaves and darker foliage compared to both the '60' variety and the '564' variety. Moreover, the new variety can be readily distinguished from related similar non-parental varieties. For example, the 'Siena Vigorosa' variety (non-patented) displays semi-double, pink colored flowers and medium green foliage, whereas the new variety displays double, red colored flowers and dark green foliage. In addition, the plant of the new variety is taller, exhibits a lower number of petals, and provides larger flowers and leaves compared to the 'Siena Vigorosa' variety.

The characteristics of the new variety have been found in Canada to be homogeneous and stable and to be strictly transmissible from one generation to another by asexual propagation through vegetative cuttings. Accordingly, the new variety reproduces in a true-to-type manner by such asexual propagation.

The new variety has been named 'VLR002', and is being marketed under the Aurora Borealis Trademark.

BRIEF DESCRIPTION OF THE PHOTOGRAPH

The accompanying photographs show as nearly true as it is reasonably possible to make the same, in a color illustration of this character, typical specimens of the plant parts of the new variety. The illustrated rose plants of the new variety were approximately two years of age and were observed during August and September of 2017 while growing outdoors in the ground on their own roots at Vineland Station, Ontario, Canada.

FIG. 1—illustrates a specimen of a 5 leaflet leaf—plan view—upper surface.

Figure 2:
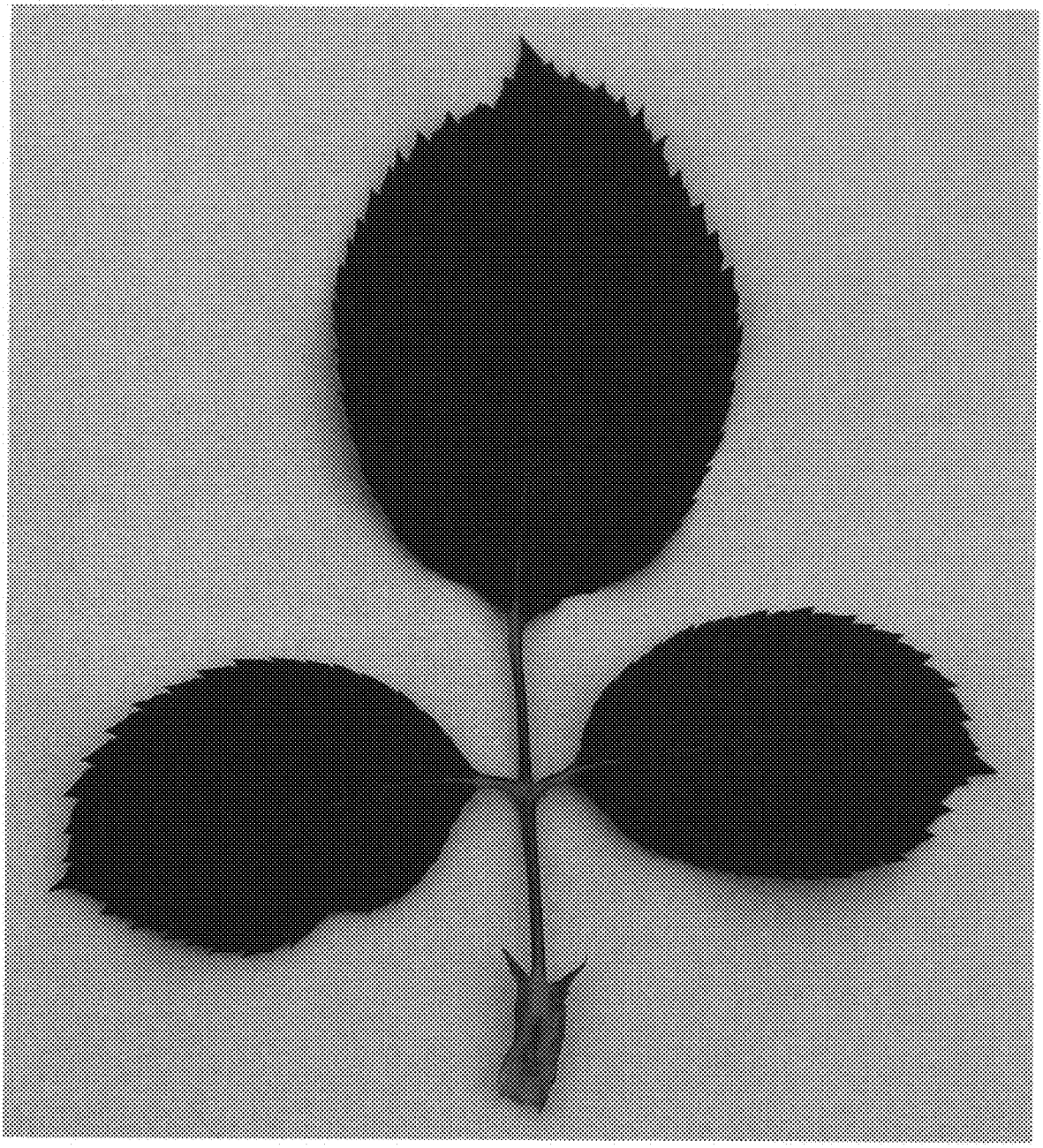

FIG. 2—illustrates a specimen of a 3 leaflet leaf—plan view—upper surface.

Figure 3:
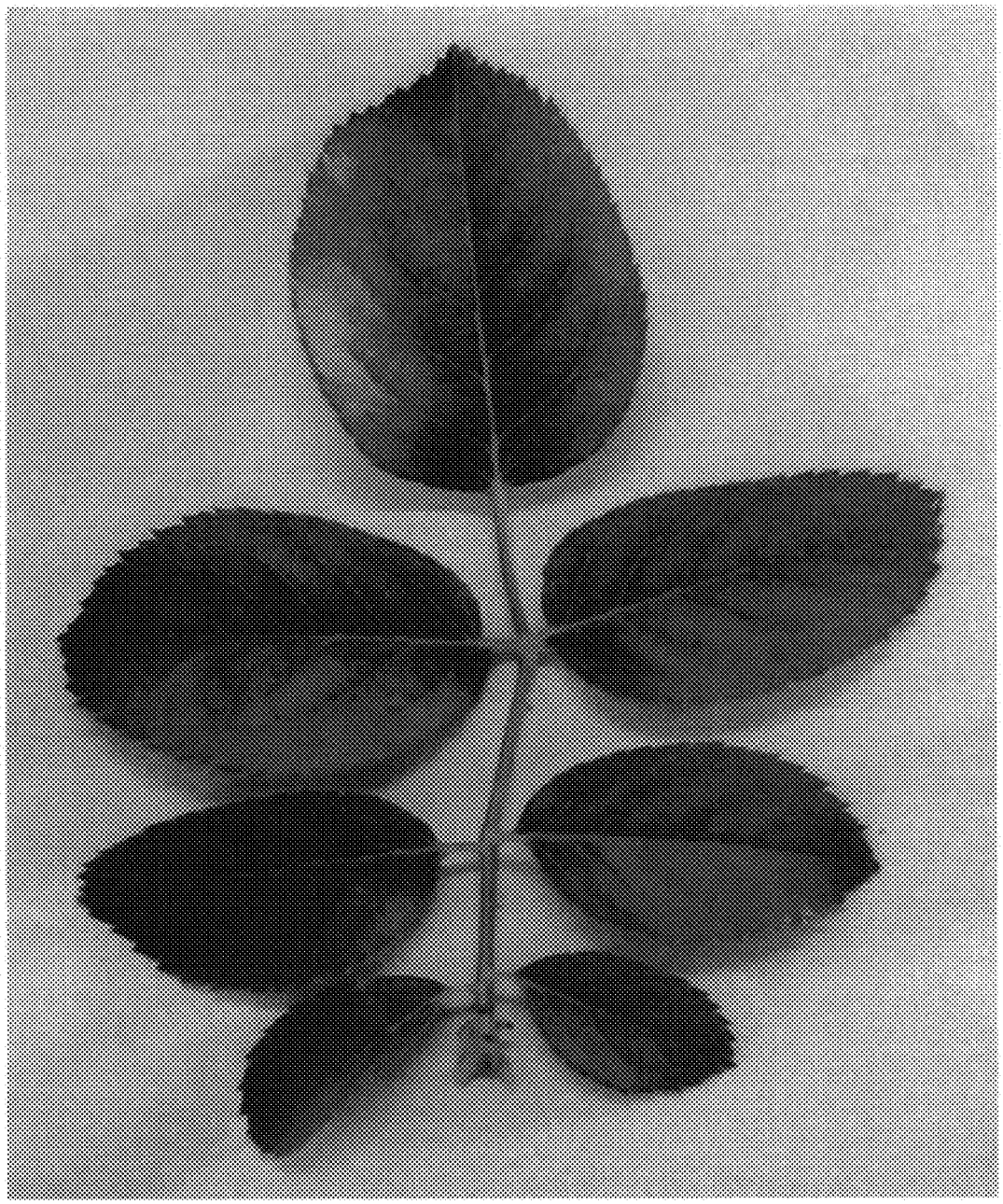

FIG. 3—illustrates a specimen of a 7 leaflet leaf—plan view—upper surface.

Figure 4:
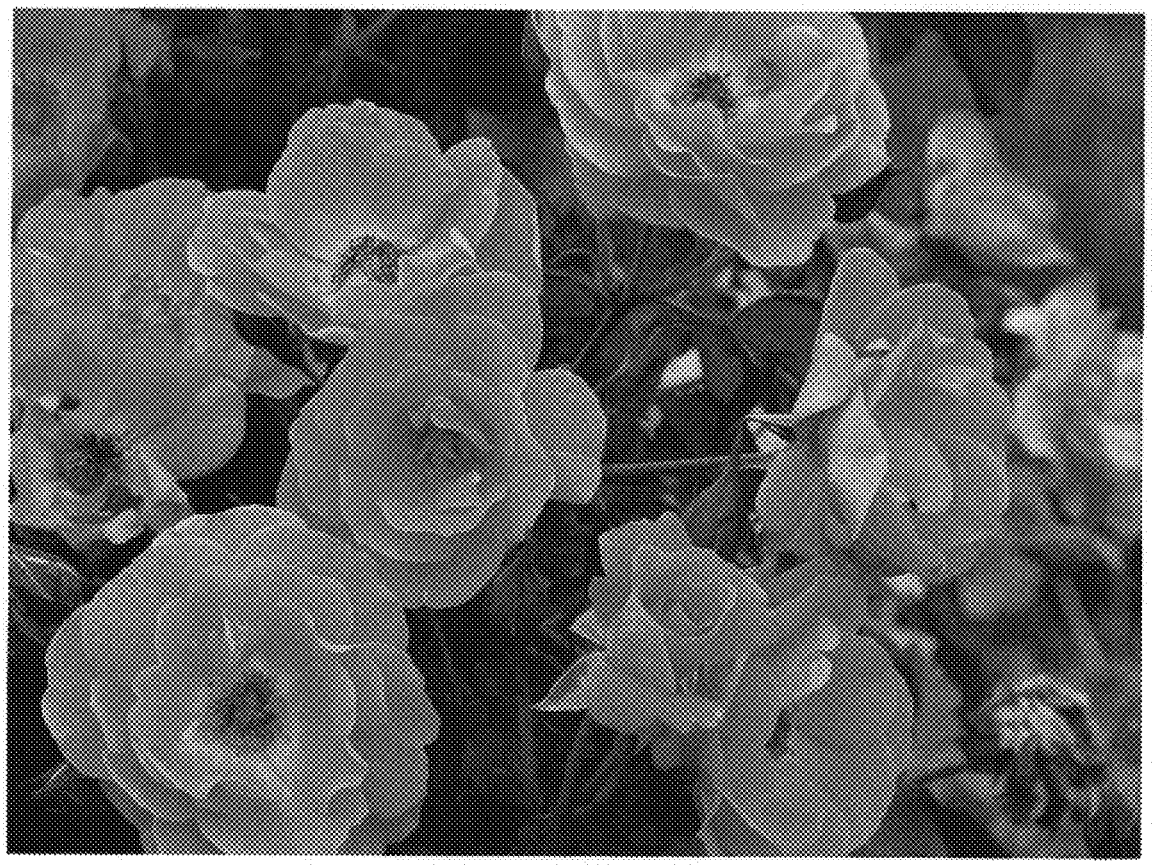

FIG. 4—illustrates a specimen of a plant growing outside; showing blossoms as various stages of opening.

Figure 5:
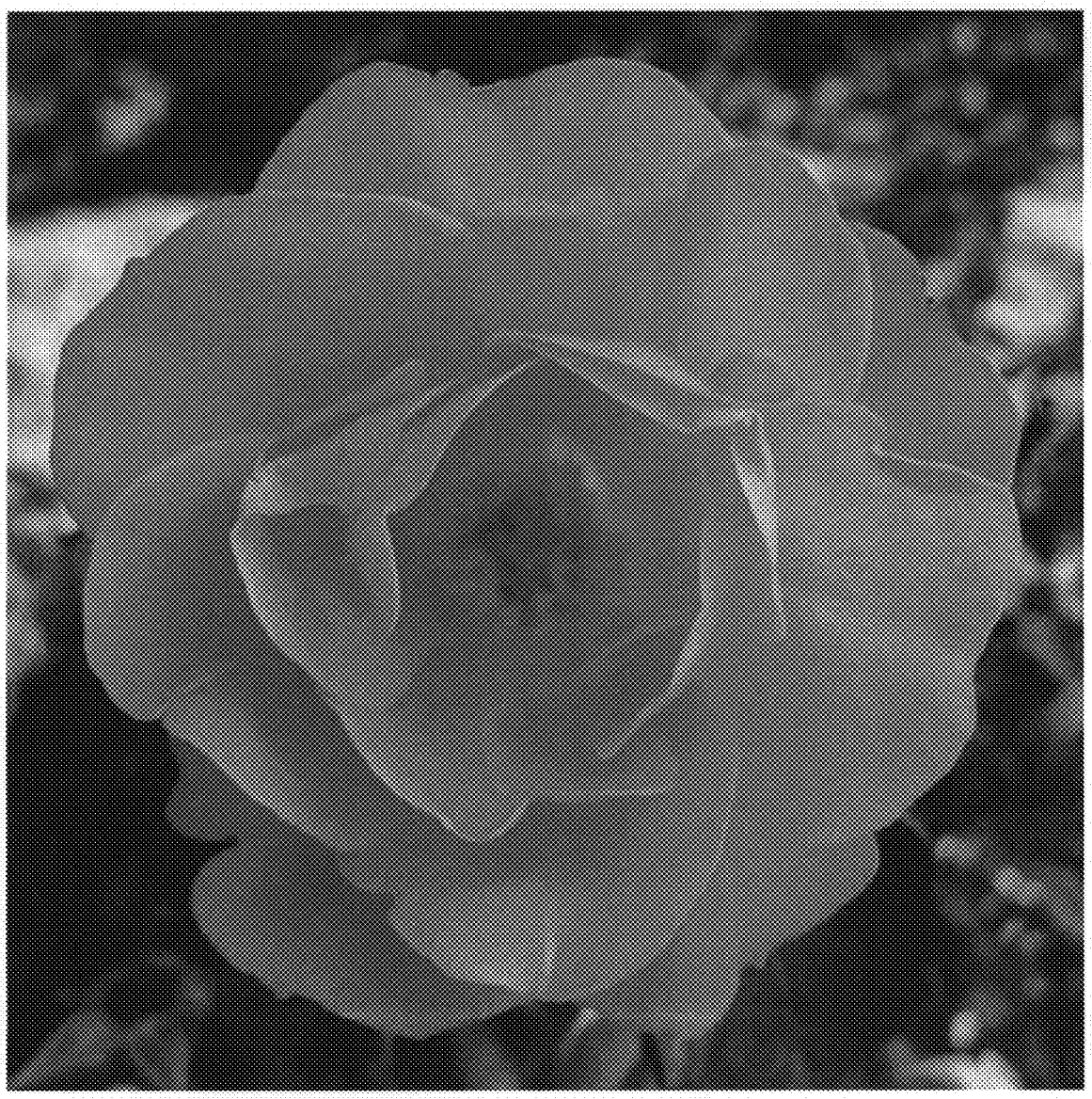

FIG. 5—illustrates a specimen of an open flower—plan view—obverse.

Figure 6:
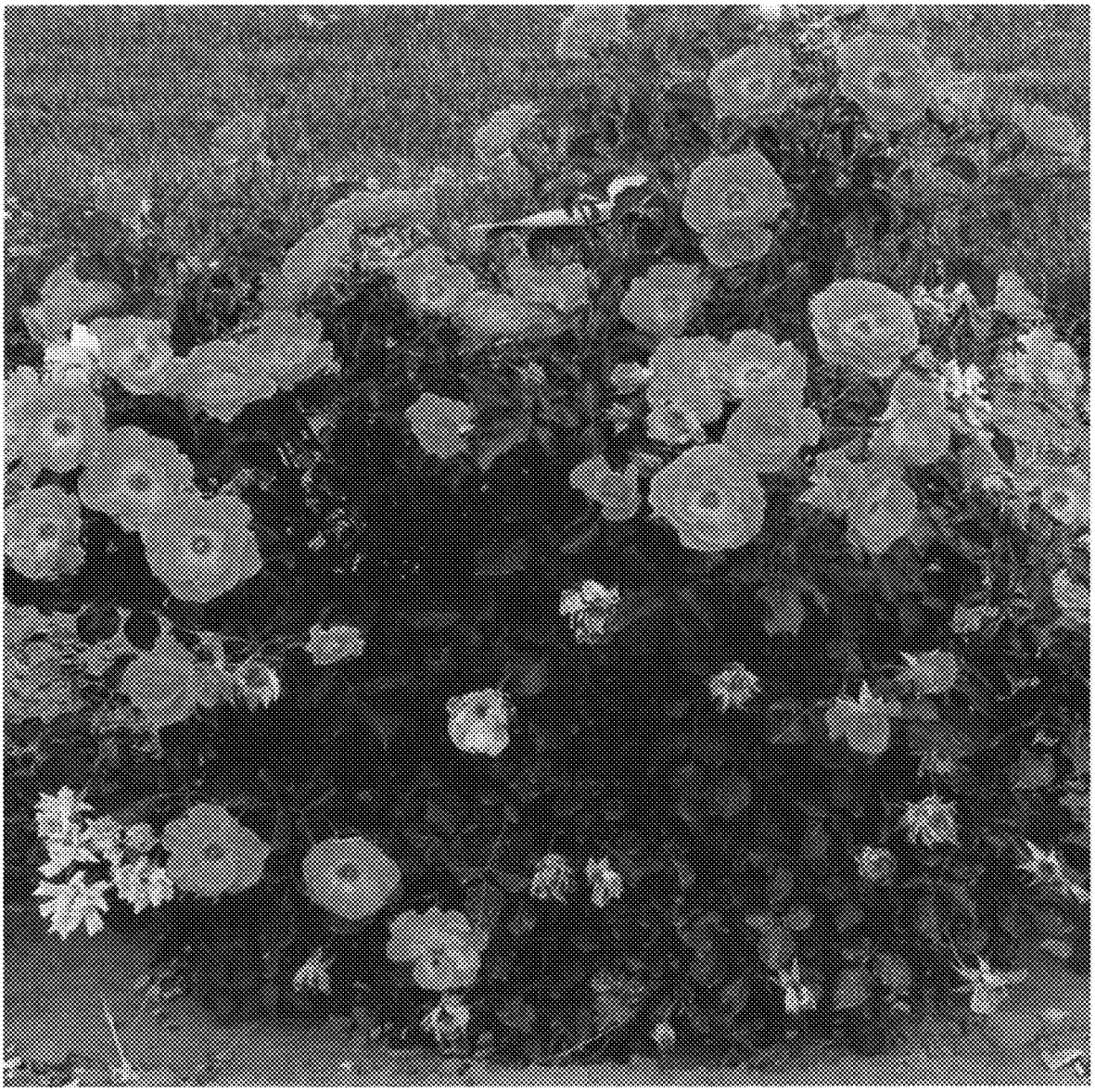

FIG. 6—illustrates an abundantly flowering rose plant growing outside.

Figure 7:
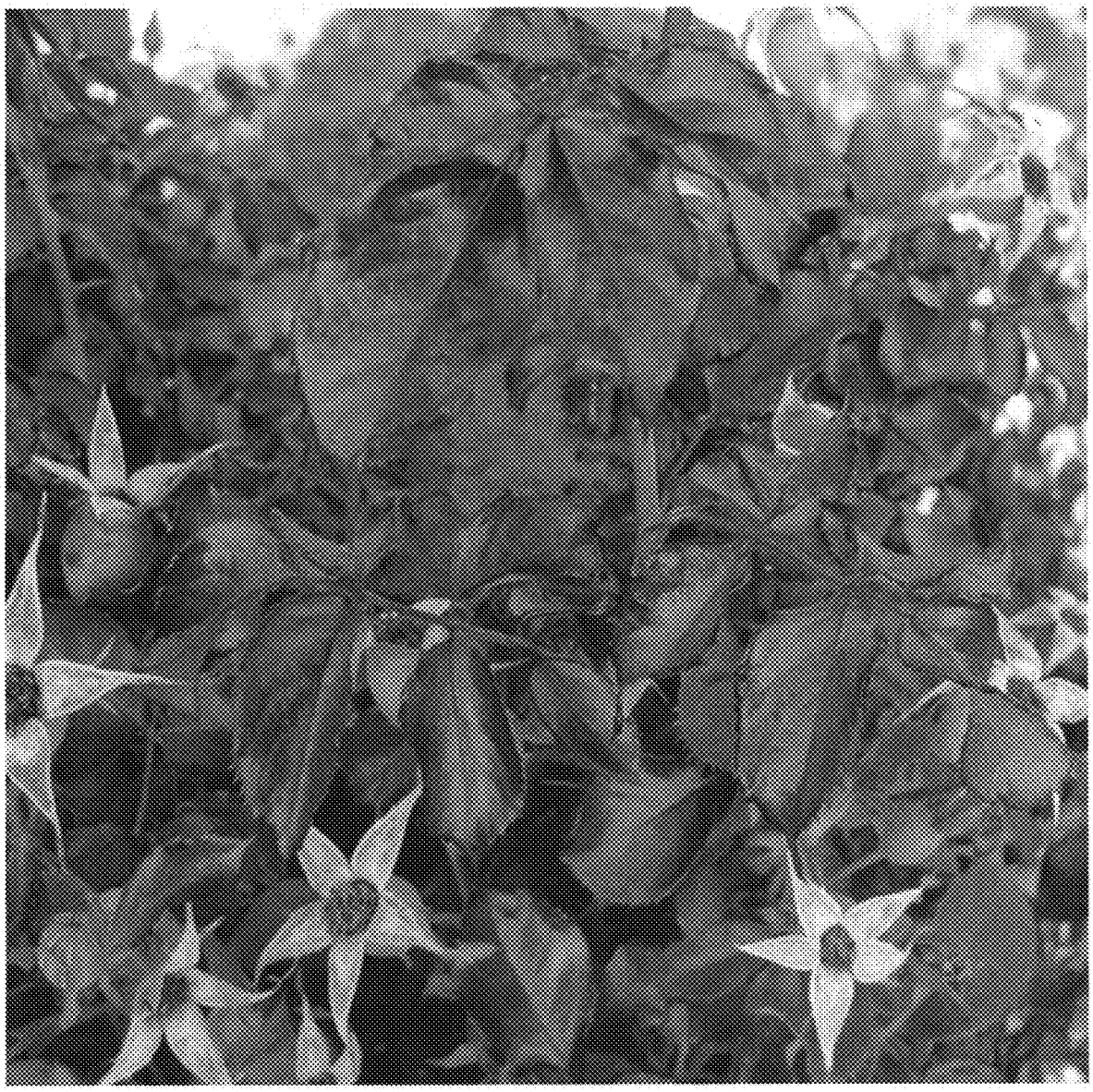

FIG. 7—illustrates the foliage of a specimen of the plant.

DETAILED BOTANICAL DESCRIPTION

The chart used in the identification of the colors is that of The Royal Horticultural Society ("R.H.S.") (R.H.S. Colour Chart, 2007). The description is based on the observation of plants two years of age during April of 2017 while growing outdoors in the ground on their own roots at Vineland Station, Ontario, Canada.

Class: Shrub Rose.

Plant:

*Growth habit*.—Semi upright bush.

*Height*.—Approximately 61 cm on average.

*Width*.—Approximately 64 cm on average.

Branches:

*Color*.—Commonly near Yellow-Green Group 144A on young stems and commonly near Green Group 138B on mature stems/old wood.

*Stems*.—Main stems: diameter is approximately 9.9 mm on average; length is approximately 62 cm on average. Secondary stems: diameter is approximately 6.0 mm on average; length is approximately 27.8 cm on average.

*Thorns*.—Young thorn: length is approximately 4.0 mm on average; diameter at base is approximately 1.9 mm on average; and color is commonly near Red Group 47C. Mature thorn: length is approximately 6.9 mm on average; diameter at base is approximately 4.1 mm; and color is commonly near Orange Group 26B.

Foliage:

*Number of leaflets*.—Typically 5, occasionally 3 or 7.

*Terminal leaflet size*.—Approximately 4.2 cm on average in length and approximately 3.0 cm on average in width.

*Lower leaflet size*.—Approximately 2.9 cm on average in length and approximately 2.0 cm on average in width.

*Overall leaf size*.—Approximately 11.6 cm on average in length and approximately 9.6 cm on average in width.

Leaflets:

*Shape*.—Ovate.

*Margin type*.—Serrate.

*Texture*.—Smooth.

*Color*.—Young leaflet: upper surface is commonly near Green Group 138A and under surface is commonly Yellow-Green Group 146B. Mature leaflet: upper surface is commonly near Yellow-Green Group 147A and under surface is commonly near Yellow-Green Group 147B.

*Venation*.—Pattern: pinnate, cross-venulate. Color: commonly near Yellow-Green Group 144B.

Inflorescence:

*Number of blossoms per cluster*.—Commonly 1-2 on average.

*Typical number of blossoms per plant*.—Commonly 75-90.

*Bloom season*.—Commonly June to October.

*Peduncle*.—Color: commonly near Yellow-Green Group 144B. Size: length is approximately 5.7 cm on average and width is approximately 2.0 mm on average.

*Sepal*.—Size: length is approximately 2.6 cm on average and width at base is approximately 7.0 mm on average. Color: upper surface is commonly near Green Group 138B and under surface is commonly near Green Group 143A. Number: commonly 5. Margin type: weak.

*Bud*.—Shape: medium ovate. Size: length is approximately 2.2 cm on average and diameter is approximately 1.3 mm on average. Color: commonly near Yellow-Green Group 146C.

*Flower*.—Form: double. Petal number: approximately 1.8 on average. Petal size: approximately 3.1 cm on average in length and approximately 3.2 cm on average in width. Petal shape: overall shape is obovate; base is round; apex is round. Petal margin type: even and smooth. Petal drop: drop clean. Size: approximately 7.2 cm on average in diameter and approximately 2.7 cm on average in depth. Color when opening: petal upper surface is commonly near Red Group 46C and petal lower surface is commonly near Red Group 45D. Color when fully open: upper surface is commonly near Red Group 46C and lower surface is commonly near Red Group 54A. Fragrance: weak. Stamen number: approximately 110-160 on average. Anther: approximately 2.1 mm on average in length, approximately 1.2 mm on average in width, sagittate in shape, and color is commonly near Yellow Group 6A. Filament: approximately 7.7 mm on average in length; approximately 0.3 mm on average in diameter; and commonly near Yellow Group 6D. Pollen: commonly a good amount and color is commonly near Yellow-Orange Group 19C. Pistil number: approximately 75-90 on average. Stigma: approximately 1.2 mm on average in length, shape is rounded, cauliflower shape, and color is commonly near Yellow-Orange Group 18B. Style:

length is approximately 5.1 mm on average, diameter is approximately 0.25 mm on average, and color is commonly light yellow.

*Receptacle*.—Shape: pitcher-shape. Size: length is approximately 8.0 mm on average and width is approximately 6.0 mm on average. Color: commonly near Yellow-Green Group 144A.

*Hips*.—Not observed at this time.

Development:

*Vegetation*.—Good healthy growth.

*Blooming*.—Continuous, June to October.

*Resistance to diseases*.—Resistance to black spot fungus *Diplocarpon rosae*.

The new 'VLR002' variety has not been observed under all possible environmental conditions to date. Accordingly, it is possible that the phenotypic expression may vary somewhat with changes in light intensity and duration, cultural practices, and other environmental conditions.

I claim:

1. A new and distinct shrub rose plant characterized by the following combination of characteristics:

(a) abundantly and continuously forms attractive double formed red blossoms, (b) exhibits a semi-upright bush growth habit, (c) forms attractive dark green foliage, and (d) is well suited for growing as attractive ornamentation in the landscape;

substantially as herein shown and described.

* * * * *